(12) United States Patent
Jimbo et al.

(10) Patent No.: US 7,806,590 B2
(45) Date of Patent: Oct. 5, 2010

(54) X-RAY CT APPARATUS

(75) Inventors: Tomohiko Jimbo, Fujisawa (JP); Hideo Iwasaki, Kawasaki (JP); Tomonao Takamatsu, Nerima-ku (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 36 days.

(21) Appl. No.: 12/402,705

(22) Filed: Mar. 12, 2009

(65) Prior Publication Data

US 2009/0232281 A1    Sep. 17, 2009

(30) Foreign Application Priority Data

Mar. 14, 2008    (JP) .............................. 2008-066367

(51) Int. Cl.
*H01J 35/10* (2006.01)
(52) U.S. Cl. .......................... 378/199; 378/4
(58) Field of Classification Search ............... 378/4–20, 378/199
See application file for complete search history.

(56) References Cited

FOREIGN PATENT DOCUMENTS

| JP | 2001-238876 | 9/2001 |
|---|---|---|
| JP | 2004-121717 | 4/2004 |

*Primary Examiner*—Courtney Thomas
(74) *Attorney, Agent, or Firm*—Turocy & Watson, LLP

(57) ABSTRACT

According to the invention, an X-ray CT apparatus includes: an annular rotator including: an X-ray tube; an X-ray detector disposed oppositely to the X-ray tube; a radiator disposed in the vicinity of the X-ray tube and dissipating heat from the X-ray tube; an air outlet provided in the vicinity of the radiator; and an air inlet provided at a position oppositely to the air outlet, a gantry cover covering peripheral of the annular rotator and having an upper air vent and a plurality of lower air vents; a plurality of fans discharging to the outside air exist in a gap between the gantry cover and the annular rotator from the air outlet; and a baffle plate provided in the gap in the vicinity of the lower air vents and controlling an air flow passing through internal space of the annular rotator and an airflow passing through the gap.

5 Claims, 8 Drawing Sheets

X-RAY CT APPARATUS

CROSS-REFERENCE TO RELATED APPLICATIONS

This application is based upon and claims the benefit of priority from Japanese Patent Application No. 2008-066367, filed Mar. 14, 2008, the entire contents of which are incorporated herein by reference.

BACKGROUND

1. Field

The present invention relates to an X-ray CT (Computed Tomography) system.

2. Description of the Related Art

An X-ray CT apparatus captures an X-ray tomography of a subject by means of X-ray radiation. In order to effectively dissipate heat originating from an X-ray tube, the X-ray CT apparatus has a structure that efficiently dissipates internally-generated heat to the outside, thereby efficiently cooling the surroundings of an X-ray detector.

A technique intended for efficiently dissipating the heat generated in the CT apparatus to the outside is proposed in JP-A-2001-238876; specifically, an air inlet is opened in a left bottom surface of a gantry when the gantry is viewed from the front; an air vent is opened in a right upper surface that opposes the air inlet with a rotary section sandwiched therebetween; and a blocking member for hindering flow of air toward the air inlet is provided along the direction of rotation of the rotary section.

A technique intended for preventing deterioration of the function of an X-ray detector, which would otherwise be caused by heat generated in a CT apparatus, is proposed in JP-A-2004-121717; specifically, a technique for placing, at the inside of the gantry front cover, a draft air duct for introducing an external air to an inner peripheral surface of a rotary section.

However, in the CT apparatus, when the rotator is stationary, the air flowed into the gantry flows through a gap between the rotator and an external cover of the gantry without passing through the inside of the rotator, thereby generating airflow that does not contribute to cooling. This raises a disadvantage of a decrease in an airflow which is present in the surroundings of the X-ray detector.

During rotation of the rotator, a high-temperature air exhaust from a radiator is emitted to the outside of the gantry cover from the air inlet opened in the lower portion of the gantry along with rotation of the rotator. The high-temperature air is again taken into the gantry from the air inlet, and hence there is a disadvantage of an increase in the temperature of the air in the gantry.

SUMMARY OF THE INVENTION

According to an aspect of the present invention, there is provided a video display apparatus including: an X-ray CT apparatus including: an annular rotator including: an X-ray tube; an X-ray detector disposed oppositely to the X-ray tube; a radiator disposed in the vicinity of the X-ray tube and dissipating heat from the X-ray tube; an air outlet provided in the vicinity of the radiator; and an air inlet provided at a position oppositely to the air outlet, a gantry cover covering peripheral of the annular rotator and having an upper air vent and a plurality of lower air vents; a plurality of fans discharging to the outside air exist in a gap between the gantry cover and the annular rotator from the air outlet; and a baffle plate provided in the gap in the vicinity of the lower air vents and controlling an air flow passing through internal space of the annular rotator and an airflow passing through the gap.

BRIEF DESCRIPTION OF THE SEVERAL VIEWS OF THE DRAWINGS

A general architecture that implements the various feature of the invention will be described with reference to the drawings. The drawings and the associated descriptions are provided to illustrate embodiments of the invention and not to limit the scope of the invention.

DETAILED DESCRIPTION

Figure 1:
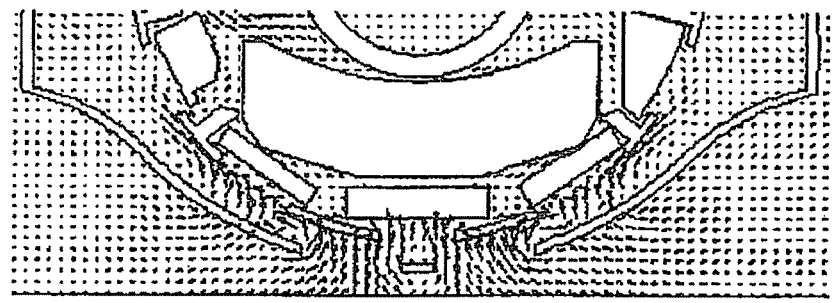
FIG. 1 is an exemplary view showing a result of analysis of a thermal fluid within a related-art CT gantry not having rectifying plates achieved when a rotator is stationary.

An X-ray CT apparatus of an embodiment of the present invention will be described hereunder by reference to FIGS. 1 through 9. Throughout the drawings, like elements are assigned like reference numerals, and their repeated explanations are omitted.

Figure 2:
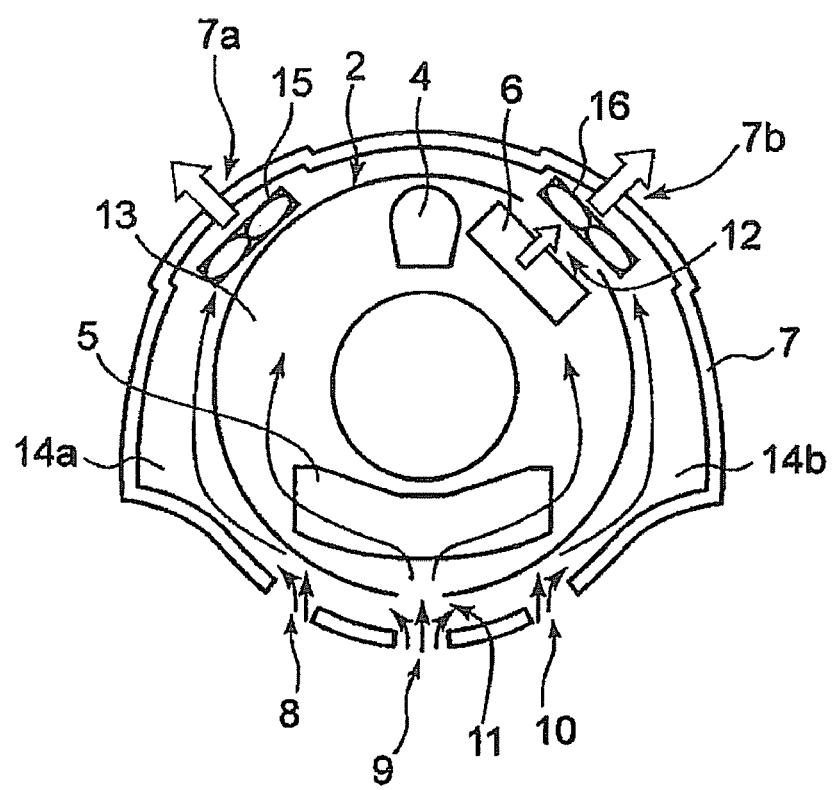
FIG. 2 is an exemplary view showing the flow of air within the related-art CT gantry not having baffle plates achieved when the rotator is stationary.

Prior to description of an embodiment, a result of analysis of a hot fluid performed by the present inventors by means of a related-art X-ray CT apparatus will be described by reference to FIGS. 1 and 2. FIG. 1 is a view showing a result of analysis of a hot fluid in a CT gantry (a velocity vector diagram) not having baffle plates achieved when a rotator is stationary. The drawings show a result of simulation obtained by use of fluid analysis software in relation to the analysis of a hot fluid in the CT gantry. As can be seen from the velocity vector, when the rotator is stationary, air flows from the air intake-and-exhaust opened in a lower portion of a gantry cover, and air flow upwardly moving from a lower position within the gantry is present in a gap between a rotator and the gantry cover. As shown in FIG. 2, the flow in the gap is exhausted to the outside of the gantry from an exhaust fan attached to a higher position on the gantry without cooling an X-ray detector that is a load in the rotator. Thus, the present inventors have come to propose an X-ray CT apparatus that decreases the airflow which flows in a gap between a rotator and a gantry cover and which does not contribute to cooling of a load in a rotator. The X-ray CT apparatus of the present embodiment will be described hereunder.

Figure 3:
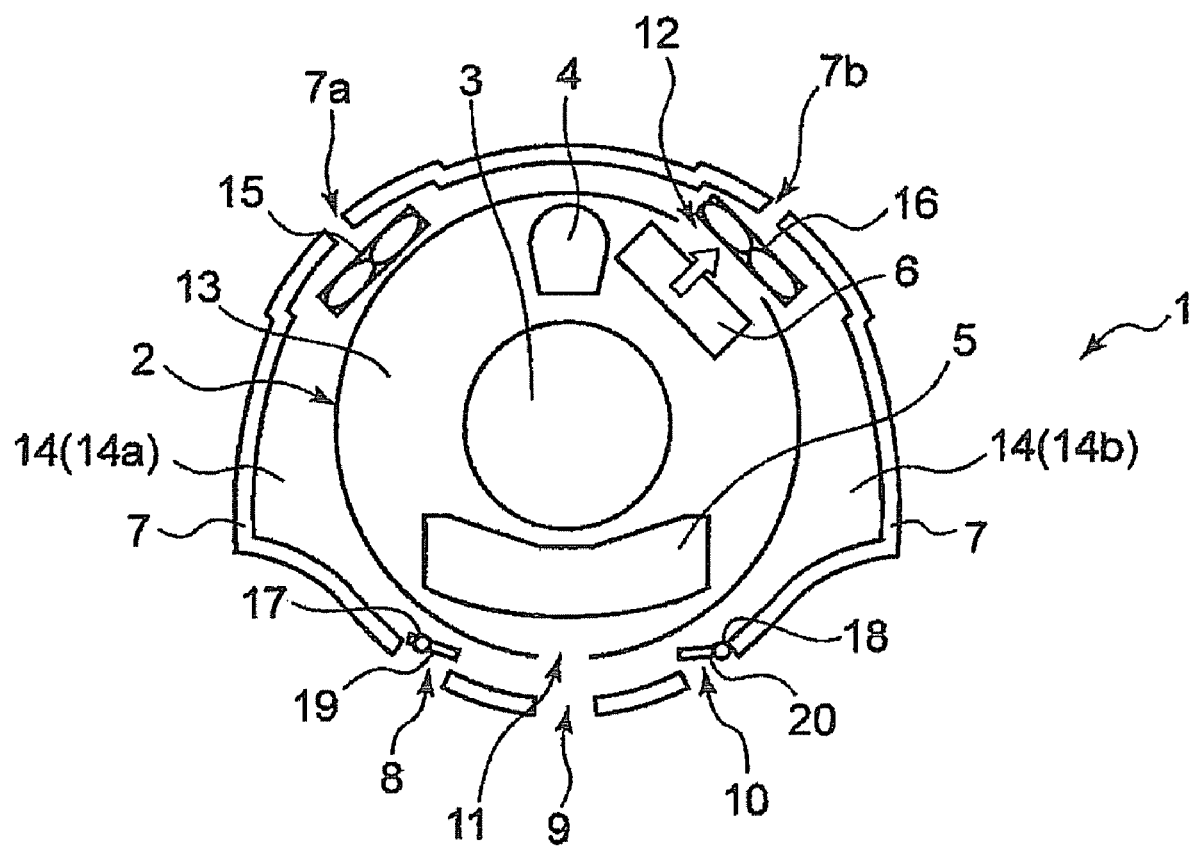
FIG. 3 is an exemplary view showing an internal configuration of a rotator of an X-ray CT apparatus of an embodiment of the present invention when viewed from the front of a rotator.

FIG. 3 is a view showing the internal configuration of the rotator of the X-ray CT apparatus of the present embodiment when viewed from the front. The drawing shows the X-ray CT apparatus whose front cover is removed. The X-ray CT apparatus 1 has a rotator 2, and a through hole 3 is opened in the rotator 2. In the rotator 2, an X-ray tube 4 for generating X radiation and an X-ray detector 5 for detecting a dose of X radiation emitted from the X-ray tube 4 and passed through a subject are disposed opposite each other with the subject interposed therebetween. A radiator 6 for dissipating heat from the X-ray tube 4 is also disposed in the rotator 2. The radiator 6 is an oil cooler that generates large amounts of heat.

Upper air vents 7a, 7b are opened in an upper portion of a gantry cover 7, and air vents 8, 9, and 10 are opened in a lower portion of the same. The air vents 8, 9, and 10 are provided in an outer periphery of the gantry cover 7 along the axial direction of the rotator 2. The rotator 2 has a vent hole 12 in the vicinity of the radiator 6, and another vent hole 11 is provided in a position opposite the position of the vent hole 12. An internal space 13 is formed in the rotator 2. A gap 14 is formed by an outer periphery of the rotator 2 and an interior surface of the gantry cover 7, and the gap 14 is in mutual communication with the upper air vents 7a, 7b, the air vents 8, 9, and 10, and the vent holes 11, 12. The gap 14 includes a gap 14a located on one side along the direction of an outer periphery of a body of the rotator 2 and a gap 14b located on the other side. Exhaust fans 15, 16 are attached to an upper cover of the gantry cover 7 and emit air in the internal space 13 to the outside.

Two shaft members 17, 18, each of which is suspended at both ends by an unillustrated frame and which is parallel to a rotary shaft of the rotator 2, are provided at edges of the air vents 8 to 10 of the gantry. A baffle plate 19 assuming the shape of a rectangular plate is attached to the shaft member 17, and another baffle plate 20 having the same shape is attached to the shaft member 18. The lengths of the baffle plates 19, 20 in the direction of a longitudinal axis thereof are essentially identical with the lengths of the air vents 8 to 10 formed in the direction of the shaft of the rotator 2. The baffle plates 19, 20 have a thickness and a size sufficient for withstanding airflow of high wind velocity. A plate material yielding a high vibration suppression effect is used for the baffle plates 19, 20. Each of the baffle plates 19, 20 has a shaft hole penetrating through the plate in the direction of its longitudinal axis, and the shaft members 17, 18 are inserted into the respective shaft holes. An opening of the shaft hole of the baffle plate 19 is positioned at one end on a transverse plane that slightly deviates left from the center along a widthwise direction. An opening of the shaft hole of the baffle plate 20 is positioned at a point on a transverse plane along a widthwise direction. These baffle plates 19, 20 are arranged in such a way that the direction of the longitudinal axis becomes parallel with the direction of the rotary shaft of the rotator 2.

By means of the configuration, airflow that enters by way of the air vents 8 to 10 opened in the lower portion of the gantry cover 7 and that flow through the gap 14 are reduced, or the airflow is blocked. Consequently, the airflow that passes by the surroundings of the X-ray detector 5 and is exhausted to the outside after having undergone heat exchange increases.

The X-ray CT apparatus 1 has an unillustrated frame that rotatably supports the rotator 2. The frame is built from; for instance, a horizontal base and a pair of vertical poles standing upright at both ends of the horizontal base. The rotator 2 is rotatably held by the frame by way of bearings, and the like. The rotator 2 has a disc with a through hole and a drum-shaped cylindrical member fitted to an outer peripheral edge of the disc. The X-ray tube 4, the X-ray detector 5, the radiator 6, and electrical equipment are attached to the disc or the cylindrical member. A CT gantry is built from the rotator 2 and the frame. The CT gantry is covered with the gantry cover 7. The X-ray CT apparatus 1 is made up of the rotator 2, the frame, and the gantry cover 7. The gantry cover 7 is made up of a front cover and a rear cover, each of which has a cutout; right and left side covers; and an upper cover having an exhaust opened therein. As a result of assembly of the covers, the X-ray CT apparatus 1 can capture an image of a subject.

Figure 4:
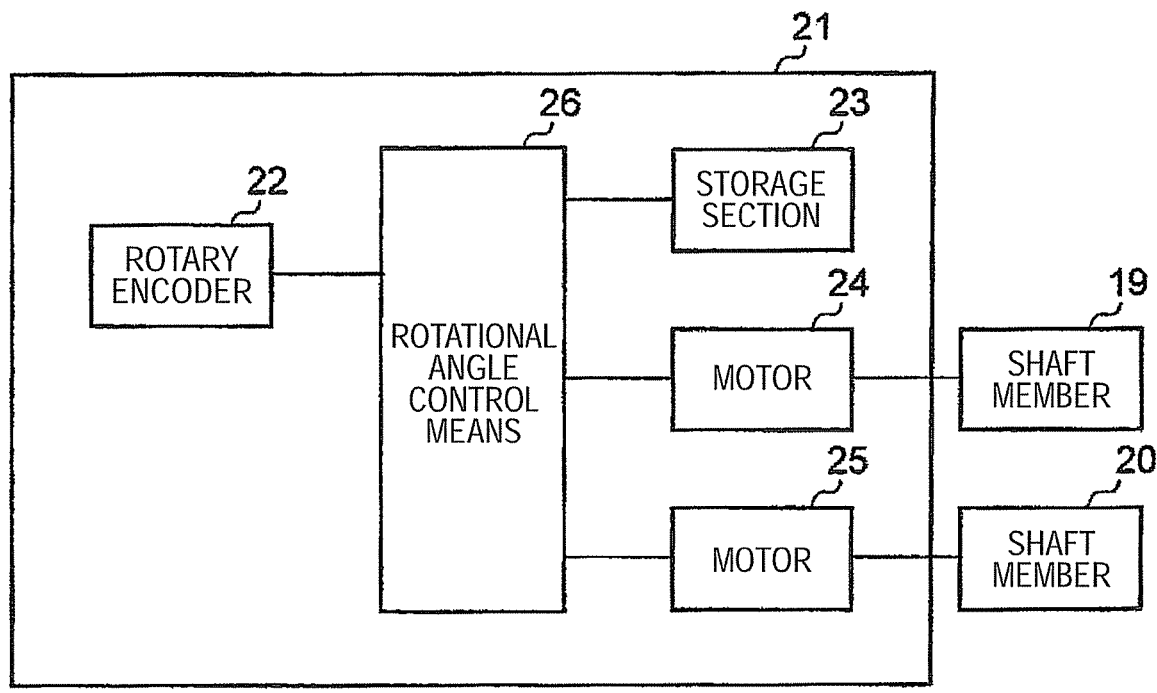
FIG. 4 is an exemplary block diagram showing an example rotation control system.

The X-ray CT apparatus 1 has a rotation control system that detects the rotational position of the rotator 2 and that controls rotational angles of the baffle plates 19, 20 in accordance with the thus-detected position. FIG. 4 is a block diagram showing an example rotation control system. The rotation control system 21 has a rotary encoder 22, a storage section 23 for storing the position of the radiator 6, a motor 24 whose shaft is attached to the shaft member 17, a motor 25 whose shaft is attached to the shaft member 18, and rotational angle control means 26 for outputting to the motors 24, 25 a signal showing amounts of opening or closing of the baffle plates 19, 20.

The rotary encoder 22 is optical rotational angle detection means that detects a rotational angle of the rotator 2. The rotary encoder 22 is attached to a position on the frame of the CT gantry, which faces an outer periphery of the cylindrical member of the rotator 2, and detects the rotational position of the rotator 2 by contacting the outer periphery of the cylindrical member. A drive signal in synchronism with the rotational position of the rotator 2 from the rotational angle control means 26 is input to the respective motors 24, 25. In accordance with the detected rotational angle of the rotator 2, the rotational angle control means 26 commands the motors 24, 25 to open or close the air vents 8, 10 of the baffle plates 19, 20. In accordance with a signal showing rotational position information output from the rotary encoder 22 and positional information about the radiator 6 previously stored in the storage section 23, the rotational angle control means 26 determines amounts of rotation of the respective baffle plates 19, 20 and generates and outputs a drive signal for driving the respective motors 24, 25. Function of the rotational angle control means 26 is implemented by a CPU, ROM, and RAM of the electrical equipment provided on the rotator 2.

By means of control operation of the rotational angle control means 26, a change is made to the airflow that is taken in by way of the air vents 8 through 10 and that is discharged to the outside from the exhaust fans 15, 16 after passing through the inside of the rotator 2 and undergoing heat exchange in the radiator 6 as well as to the airflow that is taken in by way of the air vents 8 to 10 and that is exhausted to the outside by the exhaust fans 15, 16 while taking the gaps 14a, 14b as flow channels.

Figure 5:
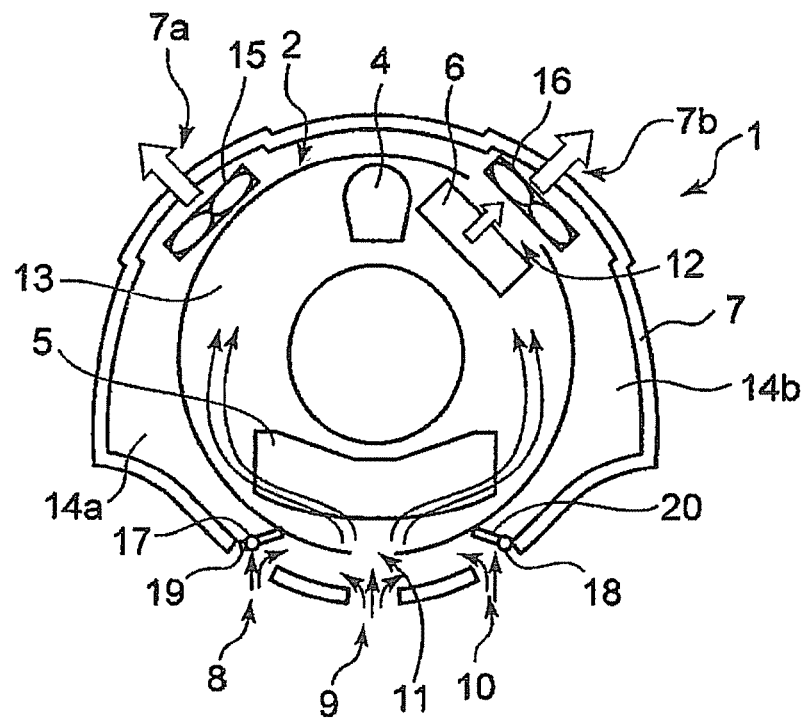
FIG. 5 is an exemplary view showing the flow of air within a CT gantry achieved when the rotator is stationary.
Figure 6:
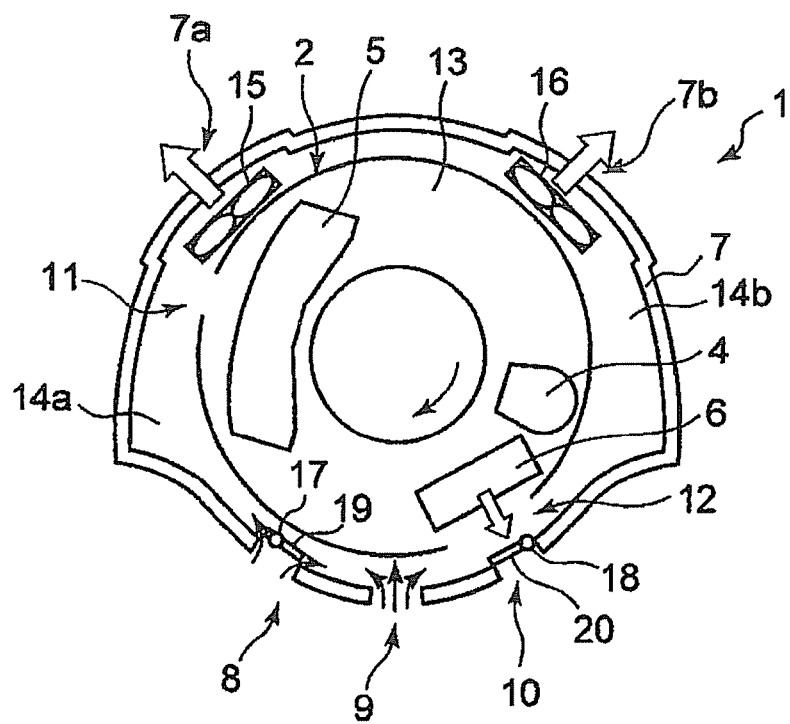
FIG. 6 is an exemplary view showing the flow of air within the CT gantry achieved when the rotator is rotating.
Figure 7:
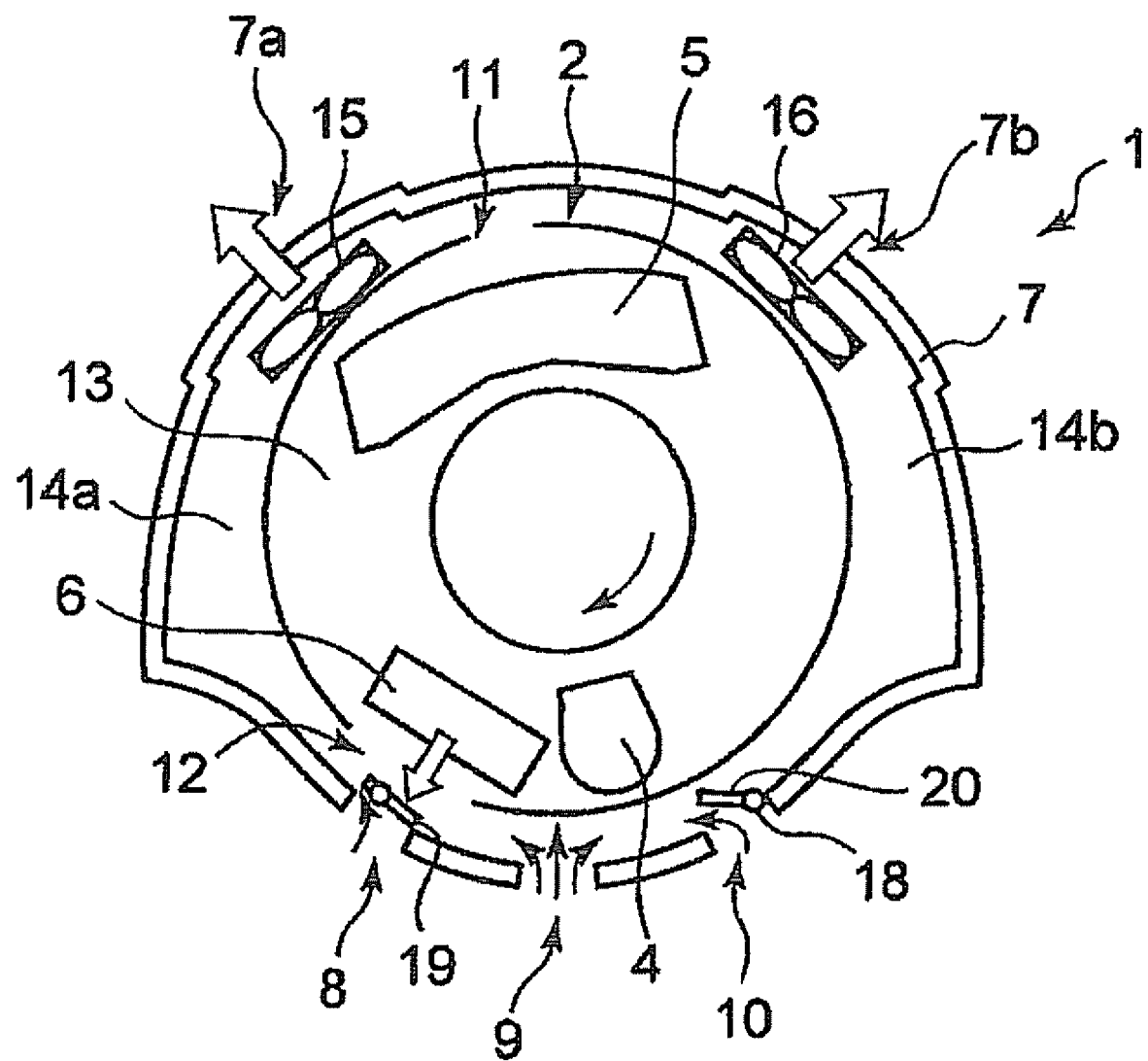
FIG. 7 is an exemplary view showing the flow of air within the CT gantry achieved when the rotator is rotating.
Figure 8A:
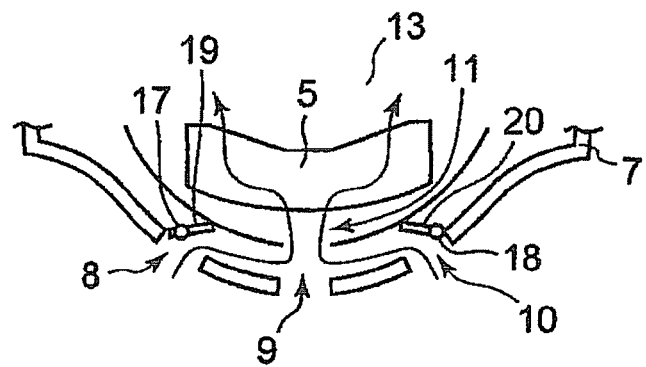
FIGS. 8A to 8C are exemplary enlarged views of the principal section of the X-ray CT apparatus for explaining operation of baffle plates.
Figure 8B:
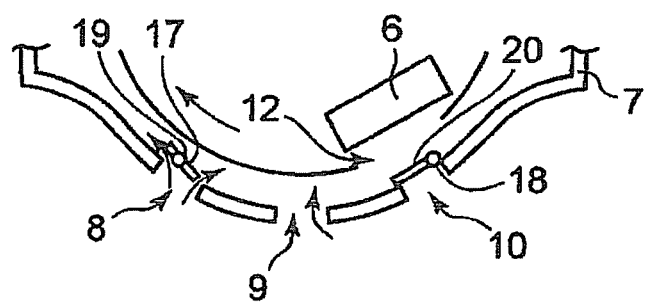
Figure 8C:
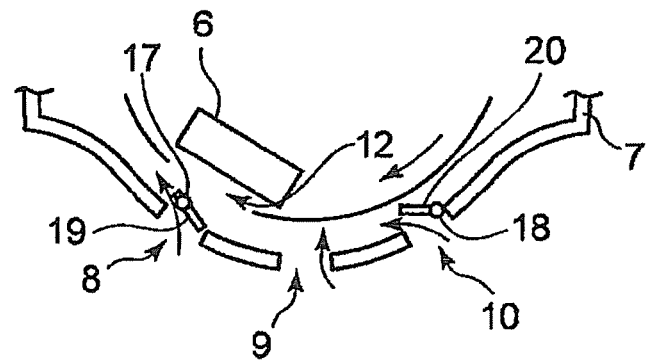

By reference to FIGS. 5 through 9, operation for cooling the CT gantry of the X-ray CT apparatus 1 of the embodiment having the foregoing configuration will be described in detail. Throughout the drawings, elements assigned the reference numerals that are the same as those previously mentioned are the same elements. FIG. 5 is a view showing airflow in the CT gantry achieved when the rotator 2 is stationary. FIG. 6 is a view showing airflow in the CT gantry achieved at the time of rotation of the rotator 2; namely, an example case where the position of the radiator 6 is in the vicinity of the air vent 10. FIG. 7 is a view showing airflow in the CT gantry achieved at the time of rotation of the rotator 2; namely, an example case where the position of the radiator 6 is in the vicinity of the air vent 8. FIGS. 8A to 8C are enlarged views of the principal section of the X-ray CT apparatus 1 for describing operations of the baffle plates 19, 20.

As shown in FIGS. 5 and 8A, when the rotator 2 is stationary, the baffle plate 19 is driven by the motor to a position along the direction of its longitudinal axis where an edge of a right side surface of the plate contacts the outer periphery of the rotator 2; and the baffle plate 20 is driven by the motor to a position where an edge of a left side surface of the plate contacts the outer periphery of the rotator 2, whereby the baffle plates 19, 20 open the respective air vents 8, 10. Under the circumstance, an air-flow channel is defined in such a way that the air entered by way of the air vents 8 through 10 is guided to the inside of the rotator 2. Inflow of the air to the gaps 14a, 14b from the air vents 8, 9, and 10 is blocked. Since the air entered from the air vents 8 through 10 opened in the lower portion of the cover flows into the rotator 2, an airflow contributing to cooling of a load in the internal space 13 increases. The air subjected to heat exchange passes by the surroundings of the X-ray detector 5 in the internal space 13 and is then exhausted to the outside. The temperature of the surroundings of the X-ray detector 5 can be hereby decreased.

When rotating, the rotator 2 performs rotation while the radiator 6 is exhausting air to the gap 14. As shown in FIG. 8B, when the radiator 6 is situated at a position shown in FIG. 6, the baffle plate 19 is driven by the motor to such an extent that an air-flow gap is defined between the right side surface of the baffle plate 19 and the cover surface and between the left side surface of the baffle plate 19 and the cover surface. The baffle plate 20 is driven by the motor such that the edge of the left side surface of the plate contacts the cover surface. The baffle plate 19 causes air to pass through the air-flow gap from the air vent 8, to thus enter the gap 14a and the gap 14b. The baffle plate 20 fully opens the air vent 10. Therefore, dissipation of the air from the vent hole 12 is blocked by an upper surface of the baffle plate 20. Since a high-temperature air is not exhausted to the lower portion of the gantry, an increase in the temperature of the air in the lower portion of the gantry is prevented. When the radiator 6 passes by the position of the air vent 10 as a result of rotation of the rotator 2, the baffle plate 20 is driven by the motor so as to open the air vent 10.

When the radiator 6 is present at the location shown in FIG. 7, the baffle plate 19 is driven by the motor, as shown in FIG. 8C, in such a way that the edge of the right side surface of the plate comes to a position which avoids the outer periphery of the rotator 2 and the air-flow gap and that the edge of the left side surface of the plate comes to a position that avoids the cover surface and the air-flow gap. The baffle plate 20 is driven by the motor in such a way that the edge of the left side surface of the plate is positioned while avoiding the cover surface and the air-flow gap. Under the circumstance, the air from the air vent 8 is guided to the gap 14a by means of the lower surface of the baffle plate 19, and exhaust of a hot air from the vent hole 12 is blocked by the upper surface of the plate. The baffle plate 20 causes the air from the air vent 10 to pass through the gap 14. Even when the radiator 6 is present at the position shown in FIG. 7, the hot air is not exhausted to the lower portion of the gantry; hence, an increase in the temperature of the air in the lower portion of the gantry is prevented. When the radiator 6 passes by the position of the air vent 8, the baffle plate 19 is driven by the motor so as to open the air vent 8.

When the radiator 6 is present at the position where the radiator faces the exhaust fan 15 as a result of further rotation of the rotator 2 and when the radiator 6 is also present at the position where the radiator faces the exhaust fan 16, a hot air exhaust is discharged from the exhaust fans 15 and 16, respectively.

Since an increase in the temperature of the air in the lower portion of the gantry is prevented under any of the circumstances shown in FIGS. 6 and 7, the hot air is prevented from flowing into the rotator 2 even when air is again taken in by way of the air vents 10 and 8 after the radiator 6 has passed by the respective air vents 10 and 8 as a result of clockwise rotation of the rotator 2.

In this regard, there is provided a description for comparison with the related-art X-ray CT apparatus not having the baffle plates 19, 20. When the rotator 2 is rotating, the hot air discharged from the air vent 10 flows into the gap 14 from the air vent 10 after the radiator 6 has passed by the position of the air vent 10. The hot air discharged from the air vent 8 flows into the gap 14 from the air vent 8 after the radiator 6 has passed by the position of the air vent 8. Therefore, the temperature of the gap 14 and the temperature of the internal space 13 are increased by the inflow of air. Since the air that is exhausted from the radiator 6 and heated is discharged in an unmodified form from the air vents 8 and 10, the discharged hot air is again taken in from the air vents 8 to 10. Since the temperature of the internal space 13 and the temperature of the gap 14 are increased by the inflow of air, the surroundings of the X-ray detector 5 cannot sufficiently be cooled in the X-ray CT apparatus that is not equipped with the baffle plates 19 and 20. In contrast, in the X-ray CT apparatus 1 of the present embodiment, the hot air exhaust from the radiator 6 is not discharged, and hence an increase in the temperature of the X-ray CT apparatus 1, which would otherwise be caused when air is again drawn by way of the air vents 8 through 10 opened in the lower portion of the cover, can be prevented.

Figure 9A:
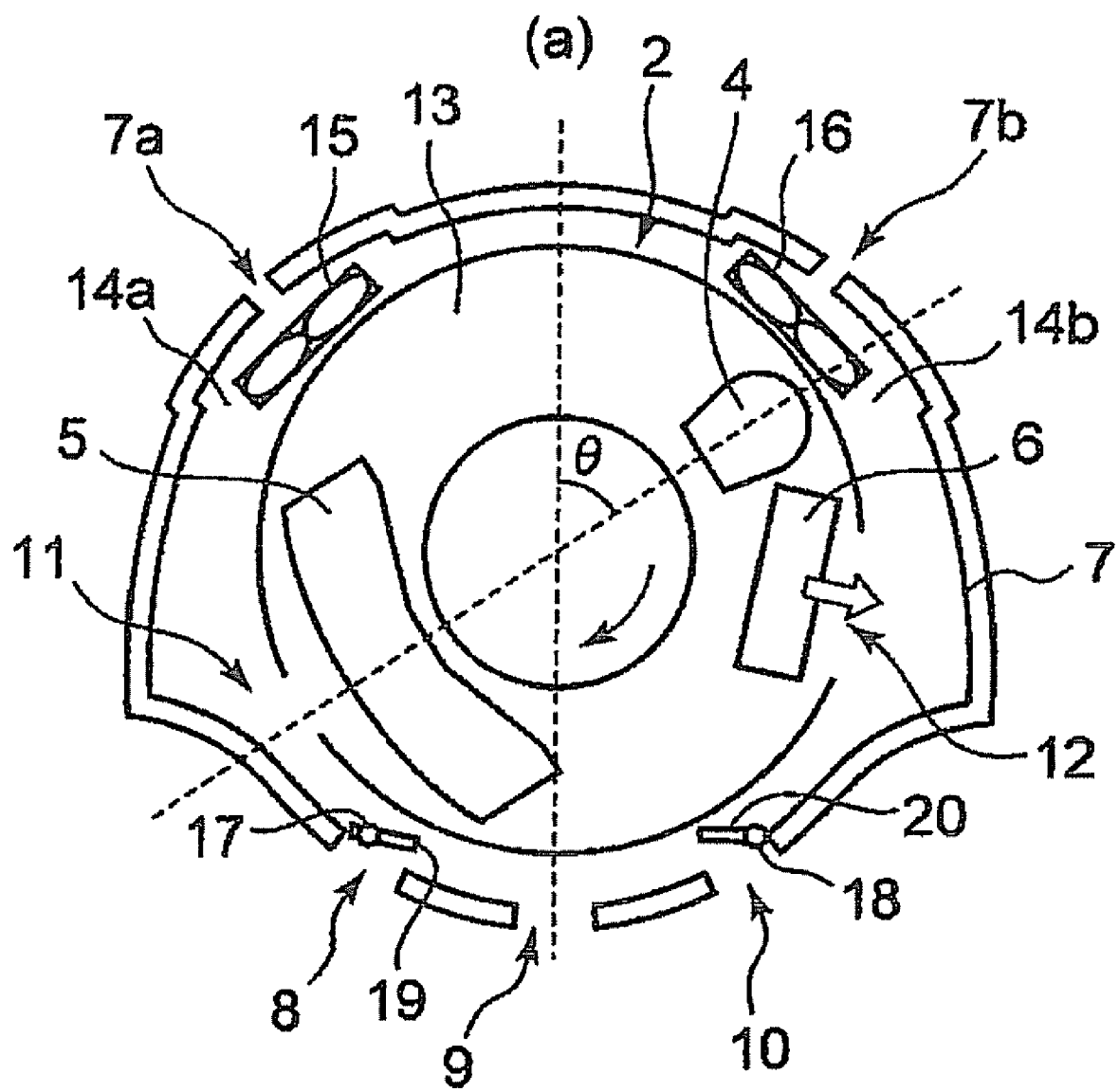
FIGS. 9A and 9B are exemplary views for describing timings at which the baffle plates open or close air vents in accordance with rotational position of a rotator.
Figure 9B:
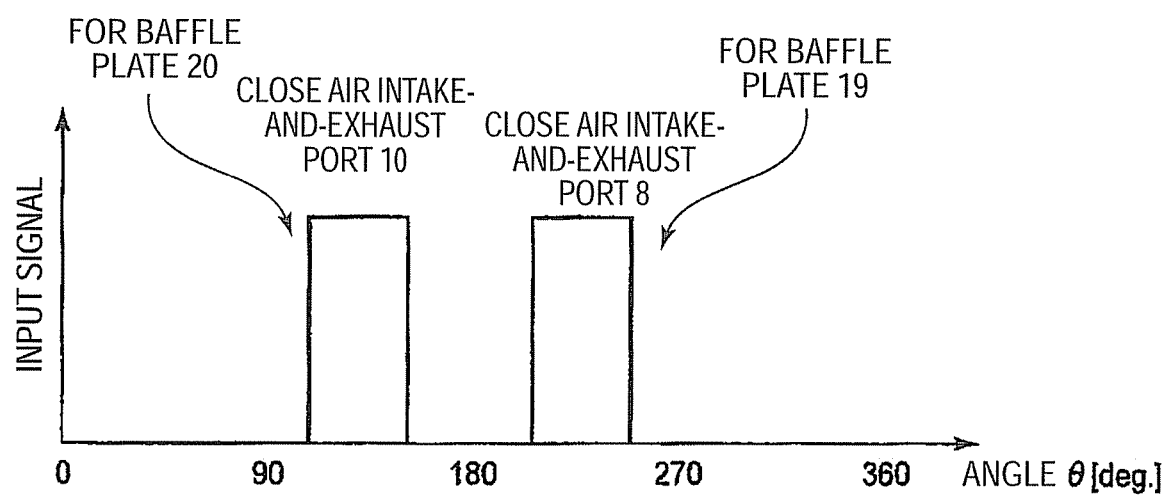

Timings at which the baffle plates 19 and 20 open and close the air vents 8 and 10 in accordance with rotational position of the rotator 2 will now be described by reference to FIGS. 9A and 9B. FIG. 9A is a view for describing the rotational angle of the rotator 2. A rotational angle θ of the rotator 2 is expressed by an angle which a plane vertical to a horizontal plane including a rotational axis forms with a plane including the rotational axis and the radiator 6. FIG. 9B is a timing chart of a drive signal input to two motors in synchronism with the rotational position of the rotator 2 when the rotator 2 is rotating (the air intake ports 8 and 10 in the drawing represent the air vents 8 and 10). A horizontal axis represents a rotational angle θ. The drawing shows a signal input from the rotational angle control means to the motor 25 for use with the baffle plate 20 and a signal input from the rotational angle control means to the motor 24 for use with the baffle plate 19.

When the rotational angle θ falls within a range exceeding 0 degree to 90 degrees, the rotational angle control means 26 does not output a signal for commanding rotation to the motors 24 and 25. When the rotator 2 rotates to a position where the radiator 6 faces the air vent 10, the rotational angle control means 26 outputs a signal for closing the air vent 10 to the motor 25 for use with the baffle plate 20. When the radiator 6 passes by the position of the air vent 10, the rotational angle control means 26 outputs to the motor 25 a signal for directing the air vent 10 in an open direction. When the rotator 2 rotates to a position where the radiator 6 faces the air vent 8 without interruption, the rotational angle control means 26 outputs a signal for closing the air vent 8 to the motor 24 for use with the baffle plate 19. When the radiator 6 passes by the position of the air vent 8, the rotational angle control means 26 stops output of the signal for closing the air vent 8 to the motor 24. During the course of the radiator 6 moving from the position passed the position of the air vent 8 to a neighborhood of the top of the gantry cover 7, the rotational angle control means 26 does not output to the motors 24 and 25 a signal for commanding rotation. As a result of a drive signal being input to the motors 24 and 25, tilt angles of the two baffle plates 19, 20 are changed. Accordingly, opening and closing of the air vents 8 and 10 are controlled in synchronism with the rotational position of the rotator 2.

As mentioned above, when the rotator 2 is stationary, the baffle plates 19 and 20 perform opening and closing operations at the gap 14; hence, the air that flows through the gap 14 without passing through the inside of the rotator 2 and that does not contribute to cooling of the X-ray detector 5 can be reduced. When the rotator 2 is rotating, the X-ray CT apparatus 1 drives the baffle plates 19, 20 by means of the motors so as to be synchronized with rotation of the rotator 2. Since the baffle plates 19 and 20 close the respective air vents 8 and 10, the air exhaust from the radiator 6 is prevented from being discharged from the air vents 8 and 10. Drawing of hot air into the air vents 8 through 10 is prevented; hence, performance for cooling the inside of the gantry achieved in the X-ray CT apparatus 1 is enhanced.

In the X-ray CT apparatus 1, the tilt angles of the respective planes of the respective baffle plates 19, 20 can be changed according to whether the rotator 2 is stationary or rotating. The air entered the gantry from the below is divided into air flowing through the inside of the rotator 2 and air passing by the outer periphery of the rotator 2; namely, the gap 14. Since the airflow passing through the gap 14 does not collide against the radiator 6, the air does not contribute to cooling of the system and is discharged, as it is, to the outside. From the viewpoint of cooling efficiency, the air entered from the air vents 8 through 10 is preferably discharged after undergoing heat exchange in the radiator 6. When a percentage of the entire volume of entered air passes through the gap 14 around the rotator, the air passing through the gap 14 is discharged without cooling the radiator 6. Therefore, the air passing through the gap 14 does not contribute to cooling operation and can be said to be useless from the viewpoint of cooling efficiency. In the X-ray CT apparatus 1 of the present embodiment, the airflow discharged from the upper portion after having passed through the channel surrounding the rotator 2 is blocked so as not to decrease the airflow existing around the X-ray detector 5. All of the entered air is hereby guided to the inside of the rotator 2, and hence cooling efficiency is enhanced.

The shaft hole of the baffle plate 19 is provided at a position that is deviated from the edge toward the center, and the shaft hole of the baffle plate 20 is provided at the edge. Provided that a baffle plate having a shaft hole provided at one end thereof is positioned in place of the baffle plate 19 and that the air vent 8 is opened or closed by the baffle plate, air flows from the below, and air entering from the above cannot be blocked. In contrast, in the X-ray CT apparatus 1, the baffle plate 19 can achieve both blocking of air and air intake.

The baffle plate 20 is positioned upstream of the rotator 2 in its direction of rotation, and the baffle plate 19 is positioned downstream of the rotator 2 in its direction of rotation. When the rotator 2 is rotating, the baffle plate 20 stays at a waiting position such that the right baffle plate 20 does not contact the rotator 2. When the left baffle plate 19 is driven by the motor to a position where the left baffle plate closes the left channel in the middle of clockwise rotation of the rotator 2, the baffle plate 19 may collide with the rotator 2. In order to enlarge the channel, the edge of the baffle plate 19 is displaced from the path of rotation of the rotator 2, thereby preventing collision between the baffle plate 19 and the rotator 2. However, hot air exhaust from the radiator 6 flows into the left gap 14a by way of the air vent 9 as well as into the gap 14. If, in the middle of rotation of the rotator 2, the rotational angle control means 26 simultaneously causes the baffle plate 20 to fully close the air vent 10 and the baffle plate 19 to fully close the air vent 8, hot air will be discharged to the gap 14a after the rotator 2 has passed by the air vent 8. In order to prevent the exhaust, the X-ray CT apparatus 1 of the present embodiment guides air by use of the baffle plate 19 in such a way that directions of the air streams become opposite to each other by means of upper and lower surfaces of the baffle plate. Entry of hot air from the lower portion into the gap 14a is also prevented. The CT gantry cooling apparatus simultaneously performs avoidance of collision of the baffle plate 19 with the rotator 2 and closing of the left air vent 8.

As mentioned above, the X-ray CT apparatus 1 of the present embodiment can reduce the airflow passing through the gap 14 without passing through the inside of the rotator 2 when the rotator 2 is stationary; and can prevent exhaust of air from the radiator 6 by way of the air vents 8 through 10 in the lower portion of the gantry cover 7 when the rotator 2 is rotating. It is hereby possible to prevent once-discharged hot air from being again drawn into the CT gantry when the rotator 2 is stationary. Further, noise due to turbulence in air, which would otherwise be caused when air is exhausted from the air vents in the lower portion, can also be prevented.

The present invention is not limited exactly to the embodiment and can be embodied in a practical stage by means of modifying constituent elements in a range where the gist of the present invention is not exceeded. The material and size of the baffle plates 19 and 20 are selected as appropriate in accordance with the size of the gantry. A structural material may also be used for the baffle plates 19 and 20.

Various inventions can be conceived by appropriate combinations of a plurality of constituent elements described in the embodiment. For instance, several constituent elements may also be deleted from all constituent elements provided in the embodiment. Moreover, constituent elements of different embodiments may also be combined appropriately.

As described with reference to the embodiment, there is provided an X-ray CT apparatus that is configured to reduce an airflow passing through a gap between an annular rotator and a gantry cover among air exhausted by way of the gap and air exhausted after passing through the inside of the rotator and subjected to heat exchange in a radiator.

According to the embodiment, the airflow passing through a gap between the annular rotator and the gantry cover is reduced.

What is claimed is:

1. An X-ray CT apparatus comprising:
   an annular rotator including:
      an X-ray tube;
      an X-ray detector disposed oppositely to the X-ray tube;
      a radiator disposed in a vicinity of the X-ray tube and dissipating heat from the X-ray tube;
      an air outlet provided in a vicinity of the radiator; and
      an air inlet provided at a position oppositely to the air outlet,
   a gantry cover covering peripheral of the annular rotator and having an upper air vent and a plurality of lower air vents;
   a plurality of fans discharging to the outside air exist in a gap between the gantry cover and the annular rotator from the air outlet; and
   a baffle plate provided in the gap in a vicinity of the lower air vents and controlling an air flow passing through internal space of the annular rotator and an airflow passing through the gap.

2. The apparatus according to claim 1, wherein the baffle plate includes a plurality of plates configured to open or to close the lower air vents in accordance with a rotational angle of the annular rotator.

3. The apparatus according to claim 1, wherein, when the annular rotator is stationary, the baffle plates is controlled to guide air drawn from the lower air vents such that an airflow passing through the gap is reduced.

4. The apparatus according to claim 1, wherein, when the annular rotator is rotating, the baffle plate closes the lower air vents in synchronization with rotation of the annular rotator to prevent hot air discharged from the radiator from being discharged outside from the lower air vents.

5. The apparatus according to claim 1, further comprising:
a shaft member supporting the baffle plate and disposed in parallel with a rotational axis of the annular rotator;
a rotational angle detector configured to detect a rotational angle of the annular rotator; and
a motor configured to rotate the shaft member;
a baffle plate controller configured to control the motor to control a rotational angle of the shaft member in accordance with the rotational angle detected by the rotational angle detector.

* * * * *